United States Patent
Gleich et al.

(10) Patent No.: US 7,758,622 B2
(45) Date of Patent: *Jul. 20, 2010

(54) METHOD AND APPARATUS FOR INFLUENCING MAGNETIC PARTICLES

(75) Inventors: Bernhard Gleich, Hamburg (DE); Juergen Weizenecker, Stutensee (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1280 days.

This patent is subject to a terminal disclaimer.

(21) Appl. No.: 10/552,802

(22) PCT Filed: Apr. 15, 2004

(86) PCT No.: PCT/IB2004/050442

§ 371 (c)(1),
(2), (4) Date: Oct. 11, 2005

(87) PCT Pub. No.: WO2004/091721

PCT Pub. Date: Oct. 28, 2004

(65) Prior Publication Data

US 2006/0213841 A1      Sep. 28, 2006

(30) Foreign Application Priority Data

Apr. 15, 2003   (EP)   ................... 03101014

(51) Int. Cl.
*A61F 7/00*   (2006.01)
(52) U.S. Cl. .................. 607/105; 607/103; 128/898
(58) Field of Classification Search ............... 606/27; 607/67, 103, 105, 113, 114; 600/12; 128/898
See application file for complete search history.

(56) References Cited

U.S. PATENT DOCUMENTS

| | | | | |
|---|---|---|---|---|
| 4,662,359 A * | 5/1987 | Gordon | .................. | 600/10 |
| 5,658,234 A * | 8/1997 | Dunlavy | .................. | 600/9 |
| 5,794,622 A | 8/1998 | Chopp et al. | | |
| 6,167,313 A * | 12/2000 | Gray et al. | .................. | 607/103 |
| 6,404,202 B1 | 6/2002 | Damadian et al. | | |
| 6,462,544 B1 * | 10/2002 | McKinnon | .................. | 324/309 |
| 6,470,220 B1 * | 10/2002 | Kraus et al. | .................. | 607/103 |
| 6,635,009 B2 * | 10/2003 | Feucht | .................. | 600/13 |
| 6,997,863 B2 * | 2/2006 | Handy et al. | .................. | 600/9 |

FOREIGN PATENT DOCUMENTS

| | | |
|---|---|---|
| EP | 0399789 A2 | 11/1990 |
| WO | 0117611 A1 | 3/2001 |
| WO | 03022360 A2 | 3/2003 |

* cited by examiner

*Primary Examiner*—Roy D Gibson
*Assistant Examiner*—Victoria W Chen

(57) ABSTRACT

The invention relates to a method and an apparatus for influencing magnetic particles in a region of action. With the help of an arrangement that has means for generating magnetic fields, a spatially inhomogeneous magnetic field is generated that has at least one zone (301) in which the magnetization of the particles is in a state of non-saturation, whereas it is in a state of saturation in the remaining zone. By displacing the said zone within the region of action, a change in magnetization is produced that can be detected from outside and that gives information on the spatial distribution of the magnetic particles in the region of action. Alternatively, the displacement may also be repeated so frequently that the region of action heats up. To improve the accessibility of the region of action, the said region is situated outside the arrangement having means for generating magnetic fields.

13 Claims, 4 Drawing Sheets

METHOD AND APPARATUS FOR INFLUENCING MAGNETIC PARTICLES

The invention relates to a method and an apparatus for influencing magnetic particles in a region of action.

Magnetic particles are relatively easy to detect and can therefore be used for examinations and investigations (particularly medical ones). A method of this kind for determining the spatial distribution of magnetic particles in an examination zone, together with the use of suitable magnetic particles for such a method and an arrangement for performing the method, are described in an as yet unpublished patent application entitled "Verfahren zur Ermittlung der räumlichen Verteilung magnetischer Partikel" ("Method of determining the spatial distribution of magnetic particles") that bears the German Patent and Trademarks Office's official number DE10151778.5. This patent application will be referred to below as D1. To allow the spatial distribution of magnetic particles in an examination zone (i.e. a region of action) to be determined, a spatially inhomogeneous magnetic field is generated that has at least one zone in which the magnetization of the particles is in a state of non-saturation, whereas in the remaining zone it is in a state of saturation. Changing the position of the said zone within the examination zone produces a change in magnetization that can be detected from the outside and that gives information on the spatial distribution of the magnetic particles in the examination zone.

Magnetic particles can also be used to heat their surroundings locally, particularly in medical hyperthermia. A method and a system of this kind for the local heating of regions of an object by variation of the magnetization of magnetic or magnetizable substances is described in an yet unpublished patent application entitled "Verfahren zur lokalen Erwärmung mit magnetischen Partikel" ("Method for local heating by means of magnetic particles") that bears the German Patent and Trademarks Office's official number DE10238853.9. This patent application will be referred to below as D2. Magnetic particles are situated in the target region (i.e. region of action) of an object. To heat the target region locally, an inhomogeneous magnetic field is generated having a pattern in space of its magnetic field strength such that a first sub-zone having a low magnetic field strength (the magnetic particles are not saturated in it) and a second sub-zone (the magnetic particles are saturated in it) that surrounds the first sub-zone and has a higher magnetic field strength are generated in the target region. The position in space of the two sub-zones in the target region is then changed for so long at a given frequency that the particles heat up to a desired temperature due to a frequent change in magnetization.

What are described in patent applications D1 and D2 are a method and an apparatus in which the object for examination is at least partly enclosed by a field-generating arrangement. The accessibility of the examination zone or target region is impaired in this way. This may, for example, give rise to states of anxiety in sensitive patients during medical examinations.

It is therefore an object of the invention to improve the accessibility of the examination zone or target region.

This object is achieved by a method for influencing magnetic particles in a region of action, which method has the following steps:

a) generation of a magnetic field having a pattern in space of its magnetic field strength such that a first sub-zone (301) having a low magnetic field strength and a second sub-zone (302) having a higher magnetic field strength are formed in the region of action, which region of action is situated outside the space surrounding the arrangement having means for generating the magnetic field, b) changing the position in space of the two sub-zones in the region of action so that the magnetization of the particles changes locally.

In the invention, a spatially inhomogeneous magnetic field is generated by an arrangement having means for generating magnetic fields. The means used for generating magnetic fields may, for example, be coils through which currents flow, or permanent magnets. The arrangement therefore generally comprises a three-dimensional structure that is composed of the coils and/or permanent magnets mentioned and that is of a certain extent in space, thus enabling a space to be defined that surrounds the said arrangement. So that the region of action through which the magnetic field flows is freely accessible from as many directions as possible, this region is situated outside the space occupied by the arrangement having means for generating magnetic fields. In contrast to this, the arrangements having means for generating magnetic fields that are described in, for example, D1 and D2, each constitute a Maxwell coil arrangement. The region of action of this arrangement is situated between the two coils of the Maxwell coil arrangement, i.e. inside the said arrangement or inside the space that surrounds the arrangement. Because of the improved accessibility of the region of action in the apparatus according to the invention, there is also a reduction in the mental stresses on a patent in medical examinations or treatments, because, for example, the patient does not feel hemmed in.

Magnetic particles such as are described in D1 or D2, for example, are situated in the region of action. The magnetic field in the first sub-zone is so weak that the magnetization of the particles deviates to a greater or lesser degree from the external magnetic field, which means that it is not saturated. This first sub-zone is preferably a spatially coherent zone; it may be a punctiform zone, but also a line or a surface. In the second sub-zone (that is, in the remaining part of the examination zone outside the first sub-zone), the magnetic field is strong enough to keep the particles in a state of saturation. The magnetization is saturated when the magnetization of practically all the particles is oriented approximately in the direction of the external magnetic field, so that when the strength of the magnetic field is further increased, the increase of the magnetization in this sub-zone will be substantially less than that in the first sub-zone in response to a corresponding increase of the magnetic field.

One possible way of changing the position in space of the two sub-zones is for a coil and/or permanent-magnet arrangement (or parts thereof) intended for generating the magnetic field on the one hand, or the object containing the magnetic particles on the other hand, to be moved relative to one another. This is a preferred method when very small objects are being examined with very high gradients (microscopy). By contrast, a preferred embodiment of the present invention does not require any mechanical movements. The position in space of the two sub-zones can be changed relatively quickly in this case, which provides additional advantages for the acquisition of signals that depend on the magnetization in the region of action.

In another embodiment of the present invention, the spatial distribution of the magnetic particles is determined. Changing the position of the two sub-zones within the region of action causes a variation in the (overall) magnetization in the region of action. If, therefore, the magnetization in the region of action or physical parameters affected thereby are measured, information on the spatial distribution of the magnetic particles in the region of action can be derived from these measurements. In practice, the particles do not have identical magnetic properties. For example, a proportion of the particles may be saturated at a magnetic field strength at which another proportion are in a state of non-saturation. This however produces an (additional) non-linearity in the magnetization characteristic that, when there is a change in the position of the two sub-zones, leads to a change in the magnetization in the region of action.

In another embodiment, signals that are proportional to the temporal change in the magnetization in the region of action are acquired. If these signals are to be as large as possible, it is important for the position in space of the two sub-zones in the region of action to be changed as quickly as possible. To acquire these signals, use may be made of a coil by which a magnetic field is generated in the region of action. Preferably however, a separate coil will be used. The change in the position in space of the sub-zones may take place by means of a temporally variable magnetic field. This being the case, a signal that is likewise cyclic is induced in a coil. However, reception of this signal proves to be difficult in as much as the signals generated in the region of action and the temporally variable magnetic field are active simultaneously; a distinction cannot therefore readily be made between the signals induced by the magnetic field and those induced by the change in magnetization in the region of action.

In yet another embodiment, the magnetic particles situated in the region of action are heated. If the spatial position of the first sub-zone is changed slightly, the magnetization of those particles that are situated in the first sub-zone, or that change from the first to the second sub-zone or vice-versa, changes when this is done. As a result of this change in magnetization, heat losses arise due to very well known hysteresis effects, or effects similar to those of hysteresis, in the particles or due to the excitation of particle movements, and the temperature of the medium surrounding the particles is increased in a heating-up region. If the first sub-zone of the magnetic field is displaced through the whole of the region of action, then the heating-up region corresponds to the region of action. The smaller the first sub-zone, the smaller is the size of the absolute minimum heating-up region.

Since only a relatively small amount of heat is produced by a once-only change in magnetization, the magnetization has to be changed more than once. The number of such changes that is required within a given period of time (i.e. the frequency), and the related increase in the temperature of the medium surrounding the particles in the heating-up region, depends on the particle concentration, on the heat produced per change (which in turn is dependent on the particle structure and the speed of reversal of the magnetization), and on the heat dissipation into the regions surrounding the examination zone.

What may be considered as magnetic particles that are suitable for the method according to the invention are, for example, those described in documents D1 and D2. No description will therefore be given of the magnetic particles at this point and instead the reader is explicitly referred to documents D1 and D2.

In another embodiment, an apparatus having a gradient coil arrangement is provided to generate the magnetic field in the region of action. This magnetic field is zero at a point along the axis of the windings and increases almost linearly at opposite polarities on the two sides of this point. Only in the particles that are situated in the zone around the point at which the field is zero is the magnetization not saturated. In the particles outside this zone the magnetization is in a state of saturation. A gradient magnetic field of this kind may be generated.

In an embodiment, it is possible not only for the region of action to be positioned outside the arrangement having means for generating magnetic fields but also for the region of action to be separated in space from the entire apparatus. In this case, a wall of a housing surrounding the apparatus is, for example, situated between the region of action and the apparatus. The method according to the invention may be performed as soon as the object containing the magnetic particles is in the region of action and close to this side of the housing. In addition, the arrangement for performing the method according to the invention that is situated in the apparatus is protected against external influences. If the enclosing housing is opaque, a patient is kept from seeing into the apparatus at the time of medical examinations, investigations or treatments and in this way the mental stress on the patient is further reduced.

In the embodiment, the zone generated by the gradient coil arrangement around the zero point of the field (i.e. the first sub-zone) is shifted within the region of action by the temporally variable magnetic field. If this magnetic field follows a suitable pattern over time and is suitably oriented, the zero point of the field can pass through the whole of the region of action in this way. When this happens, either the region of action can be heated up or the spatial distribution of the magnetic particles can be determined.

The change in magnetization that goes hand in hand with the displacement of the zero point of the field can be detected, and the spatial distribution of the magnetic particles in the examination zone can be determined from the signal measured. The coil used for receiving the signals generated in the region of action may in this case be a coil that is already being used to generate the magnetic field in the region of action. There are however also advantages in using a separate coil for reception, because this coil can be decoupled from the coil arrangement that generates a temporally variable magnetic field. Also, an improved signal-to-noise ratio can be obtained with a coil, but even more so with a plurality of coils. In analyzing the signals received, use is made of the fact that the magnetization characteristic of the particles is not linear in the zone in which the magnetization changes over from the non-saturated state to the saturated state. This non-linearity ensures that, for example, a magnetic field that varies sinusoidally in time at a frequency f causes a temporally variable induction at the frequency f (fundamental wave) and at whole-number multiples of the frequency f (harmonic waves or higher harmonics) in the zone of non-linearity. Analysis of the harmonic waves offers the advantage that the fundamental wave of the magnetic field, which field is active simultaneously to shift the field-free point, has no effect on the analysis.

For other particular embodiments, the reader is referred at this point to documents D1 and D2.

These and other aspects of the invention are apparent from and will be elucidated with reference to the embodiments described hereinafter.

Figure 1:
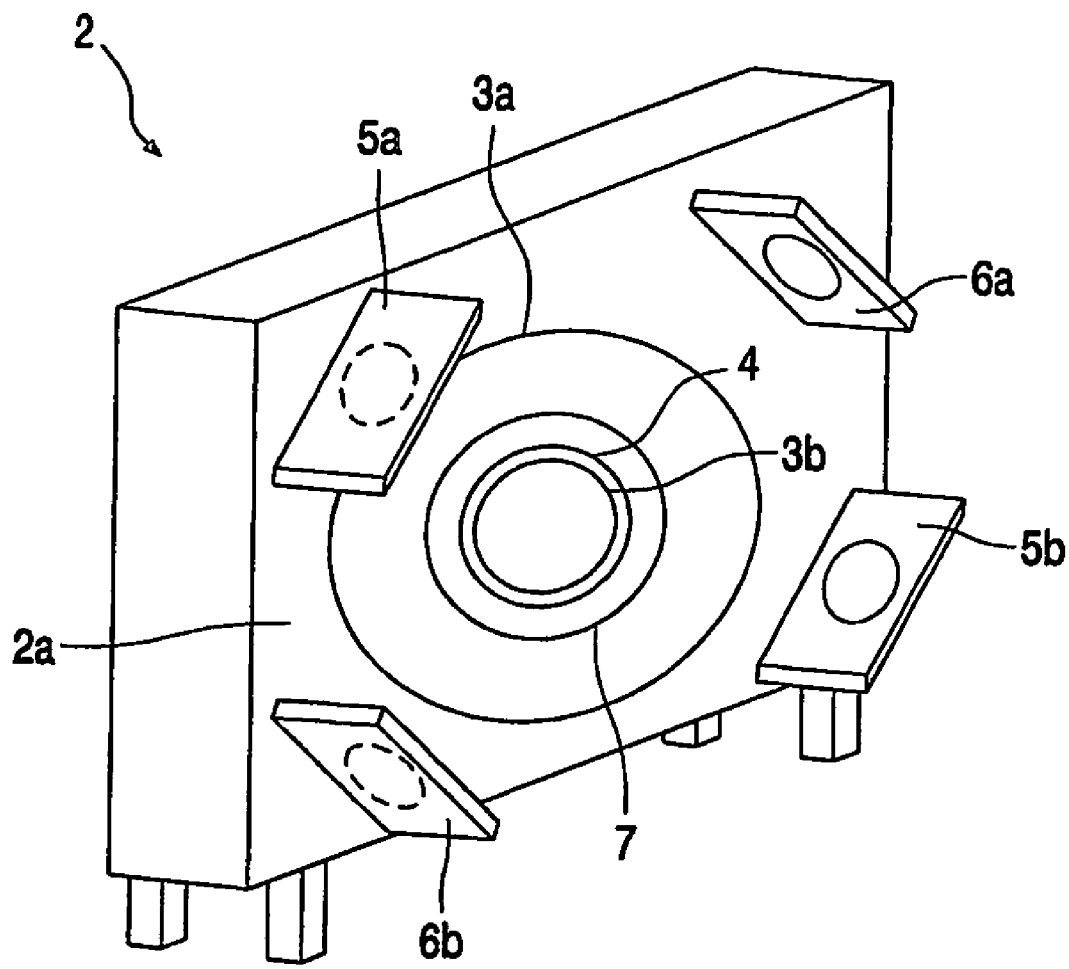
FIG. 1 shows an apparatus for performing the method according to the invention.

In FIG. 1 is shown an apparatus with which the method according to the invention can be performed. For examination purposes, a patient positions himself directly in front of the vertical side 2a of the housing 2. As an alternative, the apparatus shown may also be arranged for horizontal operation. When this is the case, the side 2a of the housing extends horizontally and the patient lies on it. For this purpose, the side 2a of the housing may be configured as a patient table, or a patient table is mounted in addition above the side 2a of the housing. Before an examination, a liquid or a meal containing magnetic particles is administered to the patient 1.

Figure 3:
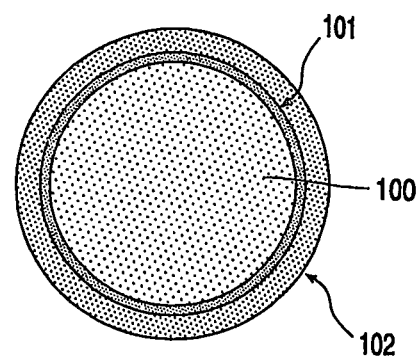
FIG. 3 shows one of the magnetic particles that is present in the region of action.
Figure 4A:
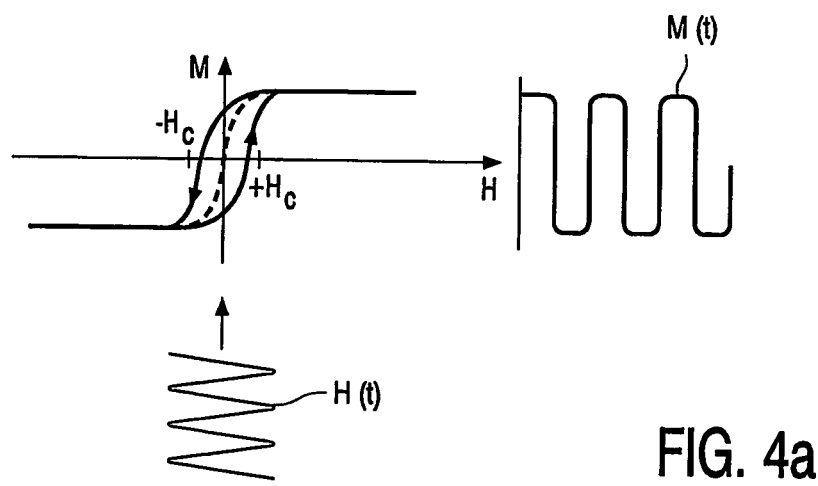
FIG. 4a and FIG. 4b show the magnetization characteristic of particles of this kind.
Figure 4B:
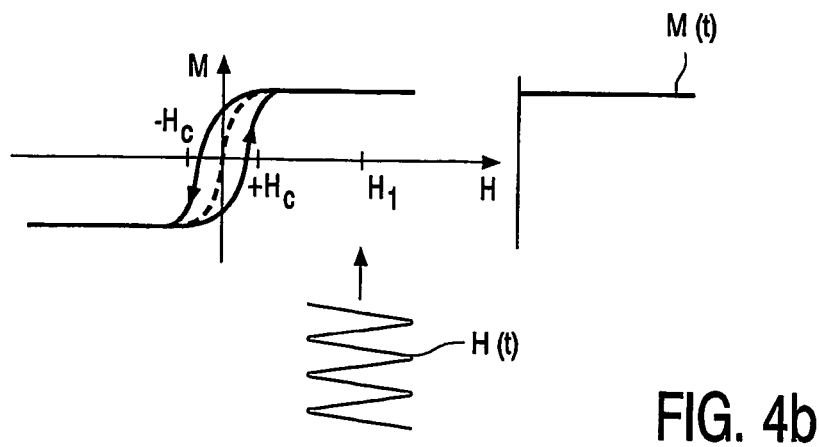

A particle of this kind is shown in FIG. 3. It comprises a spherical substrate 100, of glass, for example, which is coated with a soft-magnetic layer 101 that is, for example, 5 nm thick and that is composed of, for example, an iron—nickel alloy (for example, Permalloy). This layer may be covered, for example, by means of a coating layer 102 that protects the particle against acids. A particle of this kind is more exactly described in D1 and D2. FIGS. 4a and 4b show the magnetization characteristic, that is, the variation of the magnetization M as a function of the field strength H, in a dispersion containing such particles. It can be seen that the magnetization M no longer changes above a field strength $+H_c$ and below a field strength $-H_c$, which means that a saturated magnetization exists. The magnetization is not saturated between the values $+H_c$ and $-H_c$.

FIG. 4a illustrates the effect of a sinusoidal magnetic field H(t) if no further magnetic field is active. The magnetization reciprocates between its saturation values at the rhythm of the frequency of the magnetic field H(t). The resultant variation over time of the magnetization is denoted by the reference M(t) in FIG. 4a. It can be seen that the magnetization likewise changes cyclically, by which means a similarly cyclic signal is induced outside the coil. As a result of the non-linearity of the magnetization characteristic, this signal is no longer purely sinusoidal in form but contains harmonics, i.e. higher harmonics of the sinusoidal fundamental wave. These harmonics, which can easily be separated off from the fundamental wave, are a measure of the particle concentration.

FIG. 4b shows the effect of a sinusoidal magnetic field H(t) on which a static magnetic field $H_1$ is superimposed. Because the magnetization is in the saturated state, it is practically uninfluenced by the sinusoidal magnetic field H(t). The magnetization M(t) remains constant over time at this area. Consequently, the magnetic field H(t) does not cause a change of the state of the magnetization and does not give rise to a detectable signal that can be detected with a suitable coil.

Figure 2A:
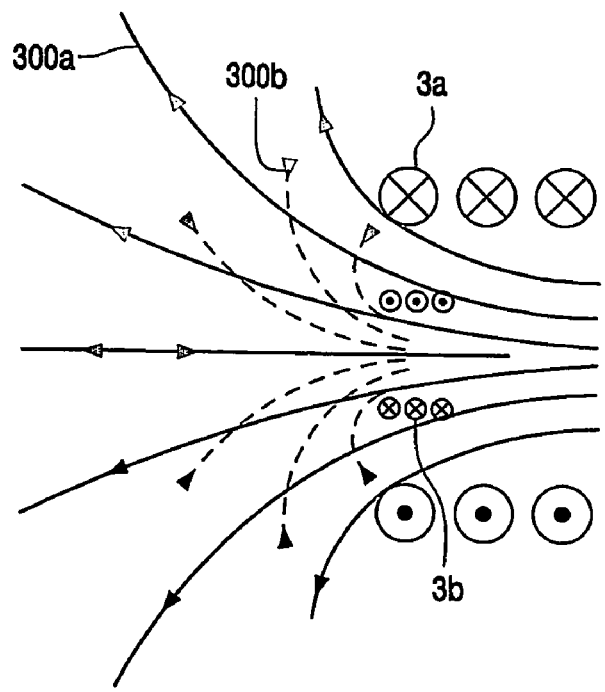
FIG. 2a and FIG. 2b show the pattern of field lines generated by the coil arrangement contained in the apparatus.
Figure 2B:
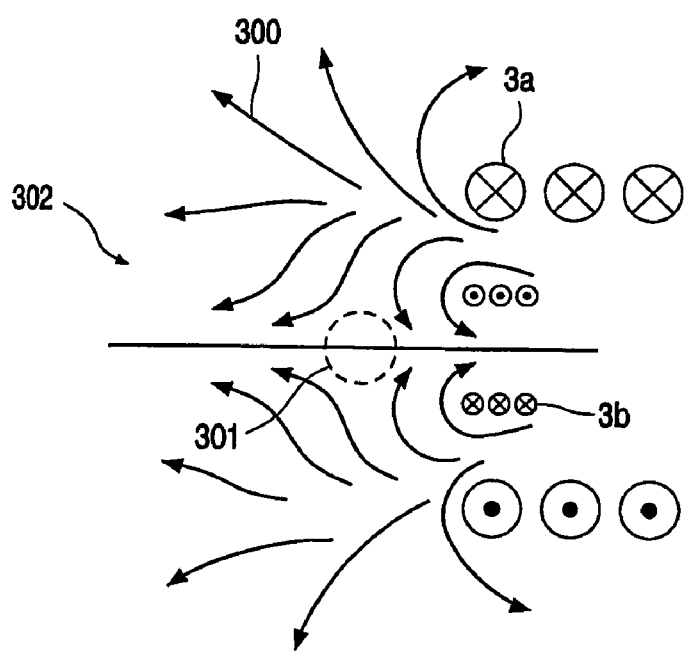

To allow information to be obtained on the spatial concentration of the magnetic particles in the object for examination (the patient in this case), there are, in and on the housing 2 of the apparatus shown in FIG. 1, coils and pairs of coils whose magnetic fields flow through the region of action. The region of action is situated in this case in front of the vertical side 2a of the housing, i.e. outside the housing 2. A first pair of coils 3 comprises the two windings 3a and 3b that surround one another co-axially, through which currents flow in opposite directions of circulation and whose common axis extends approximately perpendicularly through the vertical side 2a of the housing. The gradient magnetic field generated in this way is shown in FIGS. 2a and 2b by means of the field lines 300, 300a and 300b. The field lines 300a of the magnetic field generated by the outer winding 3a are shown as solid lines and the field lines 300b of the magnetic field generated by the inner winding 3b are shown as dashed lines. The magnetic fields from the two windings are superimposed on one another to form the magnetic field indicated by the field lines 300. This field has a gradient in the direction of the common axis of the pair of coils 3 and at one point along this axis it reaches a value of zero. The position of this field-free point along the common axis is selected in such a way that it is located outside the housing 2 and inside the region of action in which the patient is situated. Starting from this field-free point, the strength of the magnetic field increases in all three directions in space with increasing distance from the point. In a zone 301 (the first sub-zone) around the field-free point, which zone is indicated, the field strength is so low that the magnetization of magnetic particles situated in it is not saturated. In the remaining zone outside 301 (the second sub-zone 302), the magnetization of the particles is in a state of saturation.

Various parameters of the arrangement can be varied to position the field-free point along the common axis. If the intensity of the current flowing through the winding 3a is increased or the intensity of that flowing through the winding 3b is reduced, the field-free point is displaced along the common axis in the direction of the windings 3a and 3b. If on the other hand the intensity of the current flowing through the winding 3a is reduced or that of the current flowing through the winding 3b is increased, the field-free point is displaced in the opposite direction. Also, the position, and particularly the starting position, of the field-free point can be influenced by varying the diameter of the windings 3a and 3b. Furthermore, the sizing of the coil arrangement must ensure that the extent of the second sub-zone 302 in space at least corresponds to that of the region of action so that all the magnetic particles not situated in the sub-zone 301 are kept in a state of saturation.

The size of the zone 301 that determines the spatial resolution of the apparatus is dependent on the one hand on the magnitude of the gradient of the gradient magnetic field and on the other hand on the strength of the magnetic field required for saturation. For a consideration of more fundamental questions the reader is referred to documents D1 and D2.

It should be pointed out at this point that for reasons of draftsmanship the relative sizes shown in FIGS. 2a and 2b are not to scale. The sub-zone 301, for example, is shown as too large in relation to the diameters of the coils formed by windings 3a and 3b, and the cross-sections of the conductors forming the windings 3a and 3b (which may incidentally also be of the same size) are shown as too large in relation to the diameters of the windings.

If a further magnetic field is superimposed on the gradient magnetic field in the region of action, then the zone 301 shifts in the direction of this further magnetic field, the size of the shift increasing with the strength of the magnetic field. If the magnetic field superimposed is temporally variable, then the position of zone 301 changes with time and in space accordingly. To generate these temporally variable magnetic fields for any desired direction in space, three further coil arrangements are provided. A coil 4 having a winding generates a magnetic field that extends in the direction of the axis of the coils forming pair of coils 3a, 3b, i.e. horizontally. In principle, the effect achievable with this pair of coils can also be achieved by superimposing currents in the same direction on the opposed currents in the pair of coils 3a, 3b, as a result of which the current in one pair of coils will decrease and that in the other pair will increase. It may however be of advantage if the temporally constant gradient magnetic field and the temporally variable vertical magnetic field are generated by separate pairs of coils.

To generate magnetic fields that extend in space perpendicularly to the common axis of the coils 3a and 3b, two further pairs of coils having windings 5a, 5b and 6a, 6b are provided, which windings 5a, 5b and 6a, 6b are situated in respective small housings on side 2a of the housing 2. The coils forming a pair of coils are so arranged in this case that their axes are likewise situated on a common coil-pair axis.

These two coil-pair axes extend through the region of action, are perpendicular both to one another and to the axis of the coils in coil arrangement 3, and intersect the latter at a common point, preferably at the field-free point of the coil arrangement 3.

It is however also possible for the windings 5a, 5b and 6a, 6b of the pairs of coils 5 and 6 to be arranged inside the housing 2. For this purpose, the four windings 5a, 5b, 6a, 6b are, for example, arranged symmetrically about the common axis of the coil arrangement 3, with the windings forming a pair of coils being situated opposite one another. The windings may be positioned inside or outside the coil arrangement 3. The axes of the coils formed by windings 5a, 5b, 6a, 6b extend parallel or at an angle other than 90° to the common axis of the coil arrangement 3, which means that the axes of the windings forming a given pair of coils are then no longer situated on a common axis. This arrangement causes a magnetic field that has a component perpendicular to the common axis of the coil arrangement 3 to be formed, in the region of action outside the housing 2, along an arcuate region between the windings of a given pair of coils. The shape of the windings 5a, 5b, 6a and 6b need not necessarily be circular and, allow the particular arcuate magnetic field to be optimized, may also be of other shapes.

Finally, there is also shown in FIG. 1 a further coil 7 the purpose of which is to detect signals generated in the region of action. In principle, any of the pairs of field-generating coils 3 to 6 could be used for this purpose. There are however advantages in using a separate receiving coil. A better signal-to-noise ratio is obtained (particularly if a plurality of receiving coils are used), and the coil can be so arranged and switched that it is decoupled from the other coils. As an alternative, the coil 7 may also be produced in the form of an independent component that is, for example, portable and is held by the patient in front of his gastro-intestinal region.

Figure 5:
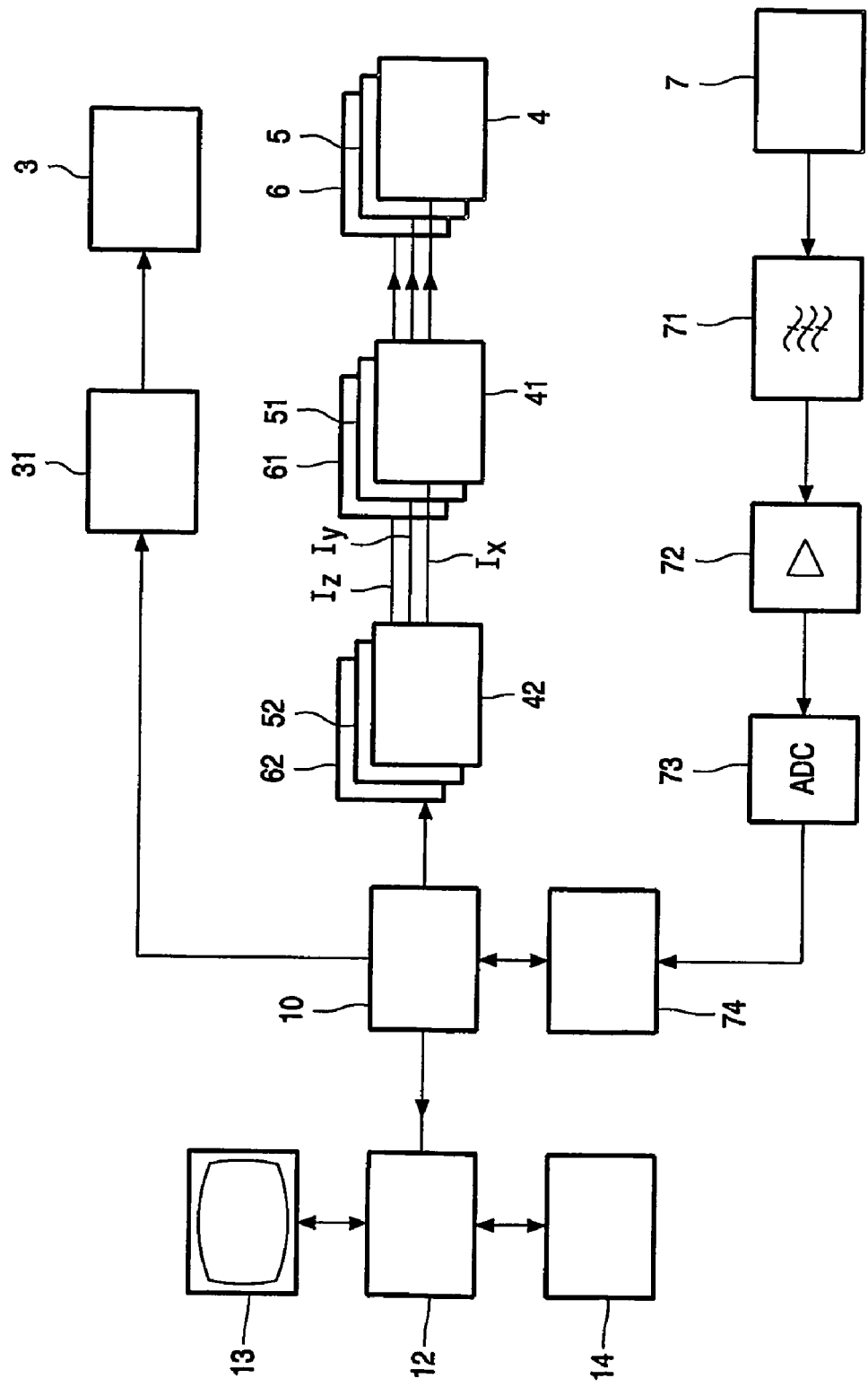
FIG. 5 is a block circuit diagram of the apparatus shown in FIG. 1.

FIG. 5 is a block circuit diagram of the apparatus shown in FIG. 1. The diagrammatically indicated pair of coils 3 (the suffixes a and b have been omitted from all the pairs of coils in FIG. 5 for the sake of simplicity) are supplied by a controllable current source 31 with d.c. current that can be controlled—and switched on and off—by a control unit 10. The control unit 10 cooperates with a workstation 12 that is provided with a monitor 13 for showing images representing the distribution of the particles in the region of action. Inputs can be made by a user via a keyboard or some other inputting unit 14.

The coils in the coil arrangements 4, 5, 6 receive their currents from current amplifiers 41, 51 and 61. The waveforms over time of the currents $I_x$, $I_y$ and $I_z$ to be amplified, which currents generate the desired magnetic fields, are preset by respective waveform generators 42, 52 and 62. The waveform generators 42, 52, 62 are controlled by the control unit 10, which calculates the waveform over time required for the particular examination procedure and loads it into the waveform generators. In the course of the examination, these signals are read out from the waveform generators and fed to the amplifiers 41, 51, 61, which generate the currents required for the pairs of coils 4, 5 and 6 from them.

Generally speaking, a non-linear relationship exists between the shift of the zone 301 from its position at the center of the gradient coil arrangement 3 and the current through the gradient coil arrangement. Moreover, all three coils must generally generate a magnetic field if the zone 301 is to be shifted in position along a straight line extending off the center. Where the waveform of the currents with time is preset, this is allowed for by the control unit, with the help of suitable tables, for example. The zone 301 can therefore be shifted through the region of action along paths of any desired shape.

The signals that are received by the coil 7 are fed to an amplifier 72 via a suitable filter 71. The output signals from the amplifier 72 are digitized by an analog-to-digital converter 73 and fed to an image-processing unit 74, which reconstructs the spatial distribution of the particles from the signals and from the position that the zone 301 is occupying at the time during the reception of the signals.

For an elucidation of various waveforms of the signals that occur in the pieces of apparatus shown in FIGS. 1 and 5, for an elucidation of the displacement of the field-free point in regions extending in two or more dimensions, and for an elucidation of the acquisition of the signals required for the reconstruction of the concentration of the particles in a one-dimensional object extending in a direction x, or even in a multi-dimensional object, such as a consideration of the mathematical questions, for example, the reader is referred to documents D1 and D2. Also to be found in documents D1 and D2 is a more extensive explanation of magnetic particles that can be used in the present case.

The advantage of the method in accordance with the invention over magnetic resonance methods consist in that it does not require a magnet that generates a strong, spatially homogeneous magnetic field. The requirements imposed as regards the temporal stability and the linearity are significantly less severe than in the magnetic resonance method, so that the construction of such an apparatus can be significantly simpler than that of an MR apparatus. The requirements imposed as regards the variation in space of the magnetic field are also less severe, so that coils with "iron cores" (a soft-magnetic core, for example, iron) can also be used, so that they become more effective and smaller.

The method according to the invention may also be performed in combination with an MR examination, in which case at least some of the coils present may be used for the reception of, or for receiving, magnetic signals.

In line with document D2, the apparatus and method illustrated in FIGS. 1 to 5 can also be used for the local heating of the regions surrounding magnetic particles. The coil 7 can be dispensed with for this purpose as no signals are detected in the local heating-up. Because the apparatus shown in FIG. 1 has similar components to that described in D2, the methods described in D2 may also be applied in the present case.

The invention claimed is:

1. A method for influencing magnetic particles in a region of action located within a subject, which method has the following steps:

introducing the magnetic particles into the region of action, generating a magnetic field using at least one coil, the magnetic field having a pattern in space of its magnetic field strength such that a first sub-zone having a low magnetic field strength and a second sub-zone having a higher magnetic field strength are formed in the region of action, which region of action is situated outside the space surrounding means for generating the magnetic field, and changing the position in space of the two sub-zones in the region of action so that the magnetization of the particles changes locally, wherein the generating step includes generating a gradient magnetic field with a gradient coil arrangement that reverses its direction and has a passage through zero in the first sub-zone of the region of action.

2. The method of claim 1, wherein the magnetic field is positionally and temporally variable to change the position in space of the two sub-zones in the region of action.

3. The method of claim 1, having the following further steps:
- acquiring signals that depend on the magnetization in the region of action, which magnetization is influenced by the change in the position in space,
- analyzing the signals to obtain information on the spatial distribution of the magnetic particles in the region of action.

4. The method of claim 3, wherein the signals that are induced by the change in the magnetization in the region of action are received and are analyzed to obtain information on the spatial distribution of the magnetic particles in the region of action.

5. The method of claim 1, wherein the position in space of the two sub-zones is changed for so long, and at a frequency such, that the region of action heats up.

6. An apparatus for influencing magnetic particles in a region of action located within a subject, comprising:
- an arrangement having means for generating a magnetic field having a pattern in space of its magnetic field strength such that a first sub-zone having a low magnetic field strength and a second sub-zone having a higher magnetic field strength are formed in the region of action, which region of action is situated outside the space surrounding the means for generating the magnetic field, and
- means for changing the position in space of the two sub-zones in the region of action so that the magnetization of the particles changes locally, wherein the means for generating the magnetic field comprise a gradient coil arrangement for generating a gradient magnetic field that reverses its direction and has a passage through zero in the first sub-zone of the region of action.

7. The apparatus of claim 6 having at least two coils arranged concentrically one within the other, through which coils currents flow in opposite directions of circulation in an operating state.

8. The apparatus of claim 6 having at least one coil and at least one permanent magnet situated inside or outside the coil.

9. The apparatus of claim 6 having a housing enclosing the arrangement, outside which housing the region of action is situated in front of a side of the housing.

10. The apparatus of claim 6 having a table above which the region of action is situated.

11. An apparatus for influencing magnetic particles in a region of action located within a subject, comprising:
- an arrangement having means for generating a magnetic field having a pattern in space of its magnetic field strength such that a first sub-zone having a low magnetic field strength and a second sub-zone having a higher magnetic field strength are formed in the region of action, which region of action is situated outside the space surrounding the means for generating the magnetic field;
- means for changing the position in space of the two sub-zones in the region of action so that the magnetization of the particles changes locally; and
- means for generating at least one temporally variable magnetic field that is superimposed on the magnetic field, for displacing the two sub-zones in the region of action.

12. The apparatus of claim 6 having
- means for acquiring signals that depend on the magnetization in the region of action, which magnetization is influenced by the change in the position in space,
- means for analyzing the signals to obtain information on the spatial distribution of the magnetic particles in the region of action.

13. The apparatus of claim 12 having a coil arrangement for receiving signals induced by the change in the magnetization in the region of action.

* * * * *